United States Patent
Stewart et al.

(10) Patent No.: US 6,882,797 B2
(45) Date of Patent: Apr. 19, 2005

(54) MULTIPLE PLATE FLUID WARMER UNIT

(75) Inventors: Thomas P. Stewart, Orchard Park, NY (US); Raymond P. Paolini, Orchard Park, NY (US)

(73) Assignee: Gaymar Industries, Inc., Orchard Park, NY (US)

(*) Notice: Subject to any disclaimer, the term of this patent is extended or adjusted under 35 U.S.C. 154(b) by 67 days.

(21) Appl. No.: 10/397,110

(22) Filed: Mar. 26, 2003

(65) Prior Publication Data

US 2004/0190884 A1 Sep. 30, 2004

(51) Int. Cl.[7] .................................................. A61F 7/00
(52) U.S. Cl. ..................... 392/470; 604/113; 219/518
(58) Field of Search ............................... 392/470, 479, 392/480; 219/518; 604/113, 93.01

(56) References Cited

U.S. PATENT DOCUMENTS

| | | | |
|---|---|---|---|
| 4,678,460 A | * | 7/1987 | Rosner .................... 604/113 |
| 4,707,587 A | * | 11/1987 | Greenblatt ................ 392/466 |
| 5,733,263 A | | 3/1998 | Wheatman |
| 5,875,282 A | | 2/1999 | Jordan et al. |
| 6,142,974 A | | 11/2000 | Kistner et al. |
| 2001/0009610 A1 | | 7/2001 | Augustine |
| 2002/0158058 A1 | | 10/2002 | Hendrix |

OTHER PUBLICATIONS

European Search Report published on Aug. 5, 2004 (3 pages).

* cited by examiner

Primary Examiner—Thor Campbell
(74) Attorney, Agent, or Firm—Roach Brown McCarthy & Gruber, P.C.; Kevin D. McCarthy (57) ABSTRACT

The present invention is directed to a parenteral fluid warming system. The system has at least first and second fluid warming bags and a warmer device. Each of the at least first and second fluid warming bags have an inlet, an outlet, a top surface, a bottom surface, and a fluid path extending between the inlet and the outlet. In a first embodiment of the present invention, the outlet from the first bag directs the fluid into the inlet of the second bag. In an alternative version of the first embodiment, the first bag and the second bag are a interconnected to each other. The warmer device has at least first and second energy reservoirs that correspond with the number of fluid warming bags. Each energy reservoir also has at least one heater unit.

22 Claims, 7 Drawing Sheets

MULTIPLE PLATE FLUID WARMER UNIT

FIELD OF THE INVENTION

The present invention relates to a medical apparatus for warming blood and other fluids to a desired temperature, prior to introduction of the fluid into a patient. The term "patient" refers to and is not limited to a dog, a horse and/or a homo sapiens.

BACKGROUND OF THE INVENTION

Gaymar Industries, Inc. is the assignee of this application, and U.S. Pat. No. 5,875,282 (the "'282 patent"). The '282 patent is directed to an apparatus for warming blood and other fluids to a desired temperature prior to introduction into a patient. In particular, the blood and other fluids flow through a counterflow fluid bag having (1) a flat counter flow pathway which (a) provides high flow performance and (b) ensures uniform, gradual and energy efficient fluid warming and (2) a pair of guide rails. The warming device contains a pair of opposed, identical heater elements separated by a receptive slot that has two guide slots, one on each side of the receptive slot. The guide rails align the bag in the warming apparatus so the bag is spaced and located precisely between the two heater elements. The pair of guide rails, integrated into the sides of the bag, are parallel to one another and provide sufficient rigidity for easy insertion of the bag into the warming apparatus. The blood warmer may also incorporate a microprocessor for precise control of the electric current provided to the heater. The microprocessor can be adjusted to have a set point ranging between ambient temperature and 60° C. and a predetermined shut off temperature point, for example, 43.5° C. Fluid temperature is measured by a RTD sensor—and in a later embodiment with a thermistor—with a thin dielectric surface layer in contact with the bag and located proximal to the fluid outlet. By monitoring the temperature of the fluid at the outlet of the bag, the temperature controller can compute and, is suppose to, provide a visual display of the fluid temperature. In one embodiment, the sensed output temperature is an input parameter to the controller of the heater elements. The device efficiently warms the fluid to a range between and including ambient temperature and 60° C. for anticipated input to a human.

SUMMARY OF THE INVENTION

The present invention is directed to a parenteral fluid warming system. The system has at least first and second fluid warming bags and a warmer device. Each of the at least first and second fluid warming bags have an inlet, an outlet, a top surface, a bottom surface, and a fluid path extending between the inlet and the outlet. In a first embodiment of the present invention, the outlet from the first bag directs the fluid into the inlet of the second bag. In an alternative version of the first embodiment, the first bag and the second bag are a interconnected to each other. The warmer device has at least first and second energy reservoirs that correspond with the number of fluid warming bags. Each energy reservoir also has at least one heater unit.

DETAILED DESCRIPTION OF THE INVENTION

The inventors admit this invention is a modification of the apparatus disclosed in the '282 patent and the modifications are designed to make the claimed apparatus more efficient. What is meant by more efficient? The inventors define more efficient as (1) increasing the flow rate of the fluid that can enter and exit the warming apparatus at a desired temperature, (2) ensuring the fluid retains the desired temperature when it enters the patient, (3) being easier to manufacture, and (4) being more reliable. The lack of efficiency is highlighted by the fact that the slow fluid rate generated by the apparatus disclosed in the '282 patent, sometimes results in the patient not receiving the fluid at the desired temperature and/or flow rate.

Figure 1:
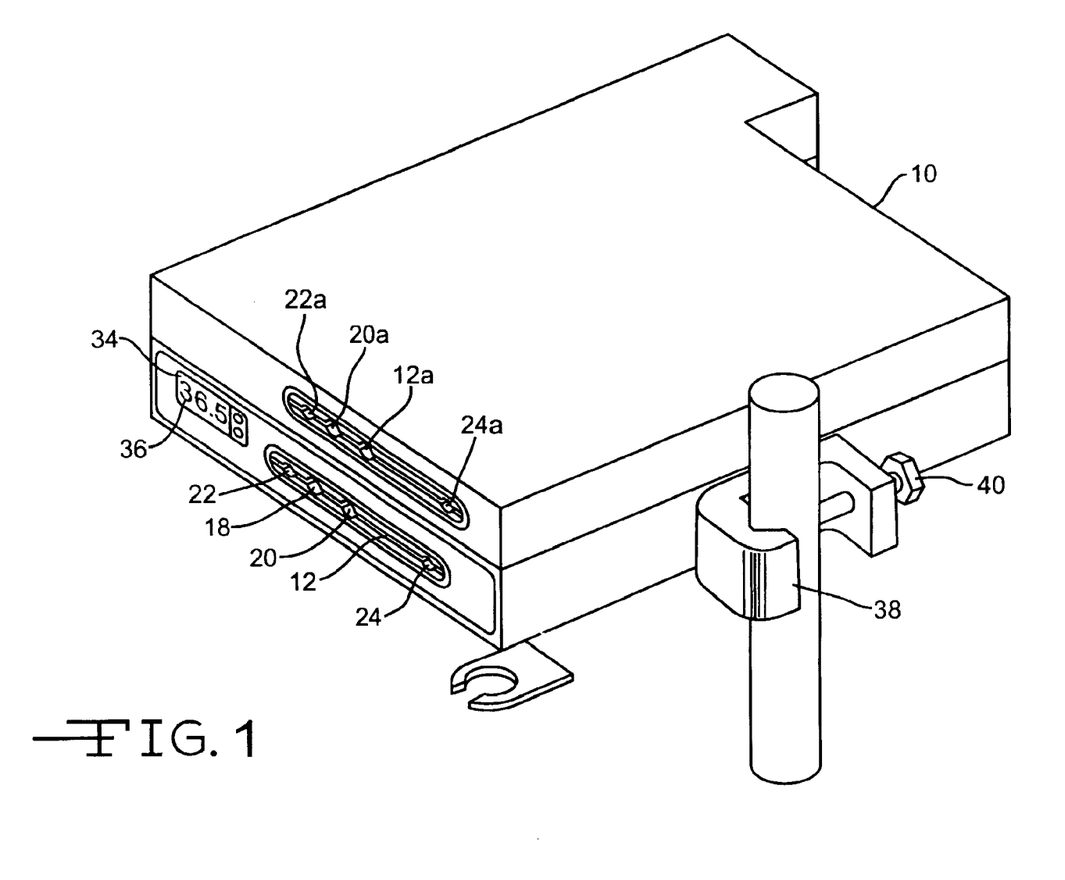
FIG. 1 is a perspective view of the blood or fluid warming device of the present invention, supported horizontally on an IV pole, only partially shown.
Figure 2:
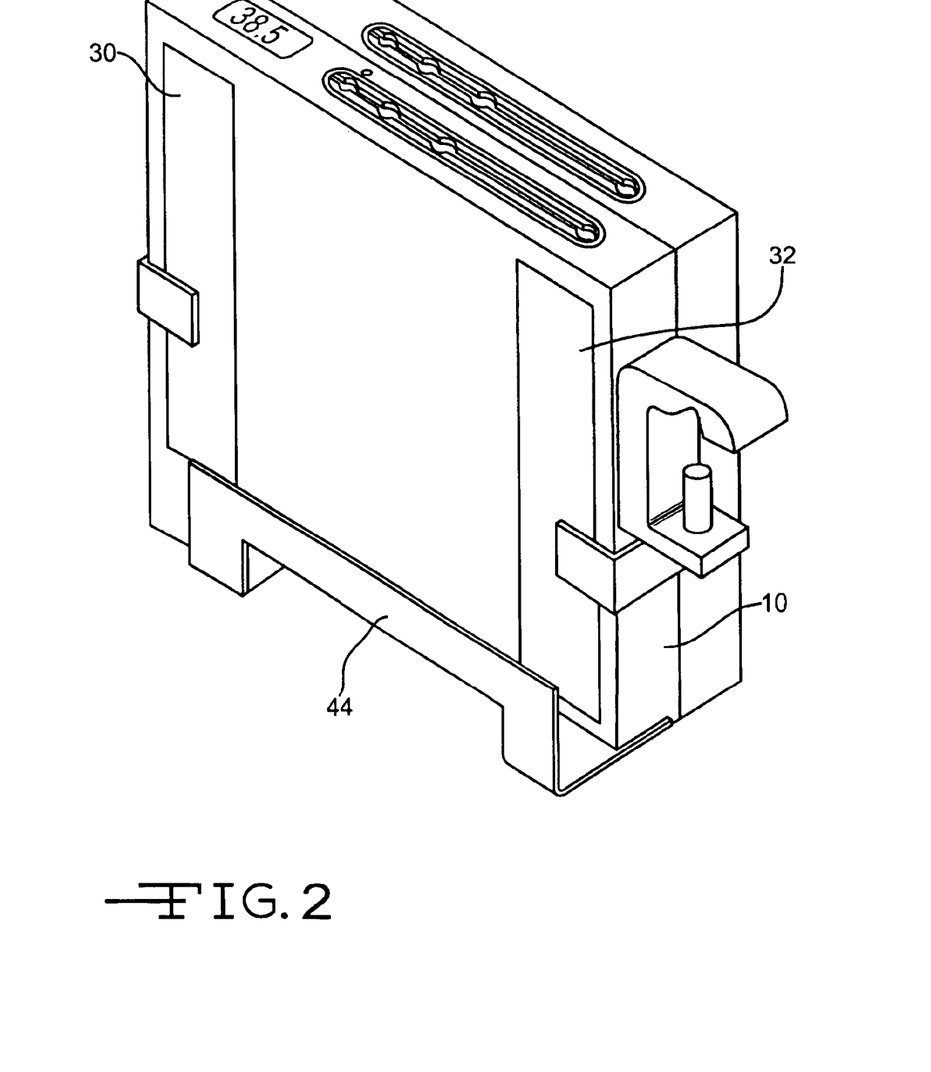
FIG. 2 is a perspective view of the present invention shown in FIG. 1, held with its bag-receiving slot extending vertically (and it can be used horizontally as well)
Figure 3:
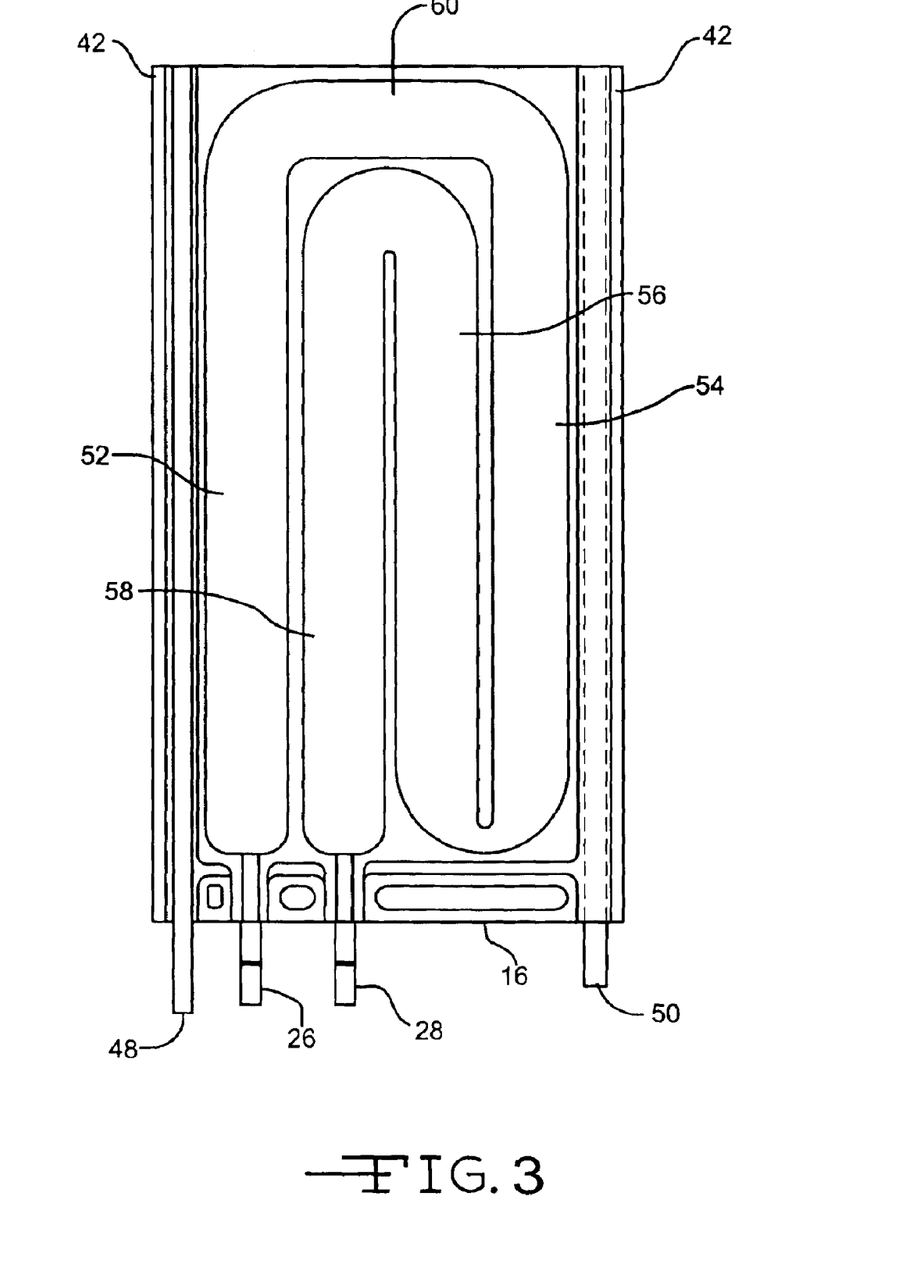
FIG. 3 is a top view of the blood or fluid warming bag intended for use with the device of FIGS. 1 and 2.

These problems are solved by the present invention. As shown in FIG. 1, a warmer controller device 10 houses electrical heating elements. The single frame instrument has a longitudinal (or alternatively in any other desired direction relative to the apparatus 10) extending slot 12 on the front 14 of the warmer 10. The slot 12 is capable of receiving a heat exchanger bag 16 (FIG. 3). The bag 16 and warmer 10 cooperate to provide a parenteral fluid warming system.

The slot 12 of the warmer 10 has integrated openings 18, 20, 22, and 24 for accommodating a tubular inlet 26, a tubular outlet 28, a first guide rail 48, and a second guide rail 50, respectively (FIG. 3). The side rails 48, 50 can be the same or different colors, and/or the same or different sizes. The front face of the warmer 10 is provided with a visual display 34 for showing, by digital readout, the temperature of the fluid near the outlet 28 in degrees Celsius (or any other defined and conventional unit for reading a temperature). For illustrative purposes, the device 10 has a digital temperature indicator 36. The device 10 can be mounted on an IV pole in a horizontal position, a vertical position, or any position in between position by adjusting the knob 40 of clamp 38 or by placing the device 10 into a bracket 44. Also with some embodiments, it can be placed in the x-ray table slot of an operating room. In addition, the device may be provided with slip resistant foam 30 and 32 to prevent undesired slippage.

FIG. 3 shows a plan view of the heat exchanger blood/fluid warming bag 16, which can be rigid or flexible. Tubular openings 42, located at outer edges of the bag 16, can sealingly contain the guide rails 48 and 50. The rails can be made from (a) independent rigid plastic that is incorporated into the bag as illustrated above, or (b) a part of the bag. The rails can be planar or any three-dimensional shape. The rails can be formed by conventional vacuum processes or even molded. In any case, the rails provide structure, rigidity, and support to the heat exchanger bag 16. Rails 48 and 50 can be color coded and may be of different or same diameters, cross-sections or shapes to engage with the warmer 10. The rails 48, 50, mate with guide channels or slots, 22 and 24 respectively, located in warmer 10. The guide channels 22 and 24 are parallel to one another to ensure smooth insertion of the bag or heat exchanger 16. These guide channels 22, 24 allow easy insertion of the bag or heat exchanger 16 into device 10. In addition, a guide tubular inlet 26 and tubular outlet 28 help maintain precise registration and alignment of the bag with respect to the heater elements contained within device 10. The rails 48 and 50 when inserted into the warmer 10 ensure the bag 16 is stretched across at least one planar heater element (or pad) 92 in the warmer 10. The rails 48, 50 also ensure the bag or heat exchanger 16 physically contacts or is close to a temperature sensor 80 at the fluid outlet 28 to facilitate uniform heating. The conventional exchanger (blood/fluid warming) bag 16 is constructed of various materials and thickness. In one embodiment, the materials are four thousandth of an inch (0.004") thick polyethylene. In others, the material can be more rigid material than the above polyethylene or alternatively used in conjunction with the above polyethylene. Alternatively, if the bag 16 is made of flexible material, the more rigid material can be used as a support between the rails to provide more rigidity. Heat sealing and/or rf sealing techniques familiar to those skilled in the art are used for construction of portions of the bag 16. For example, the inlet, the outlet, the guide rails (in some cases) and the serpentine and/or tortuous fluid flow path between the inlet and the outlet can all be formed using heat and/or rf sealing particular portions of the bag.

FIG. 3 shows the sealing pattern used in the manufacture of a preferred embodiment of the bag. The fluid path depicted in FIG. 3 has five sections, four parallel portions 52, 54, 56 and 58 to each other and one perpendicular segment 60. The fluid inlet 26, which is open to the fluid path 52, allows cooler fluid into section 52 then to segment 60, onto portions 54, 56 and then to 58 which is open to outlet 28. Each fluid pathway is and can have various widths, preferably equal widths. Fluid pathway inlet portion 52 is adjacent to fluid pathway outlet portion 58 to facilitate uniform heat distribution by a thermal counter balance.

Figure 4:
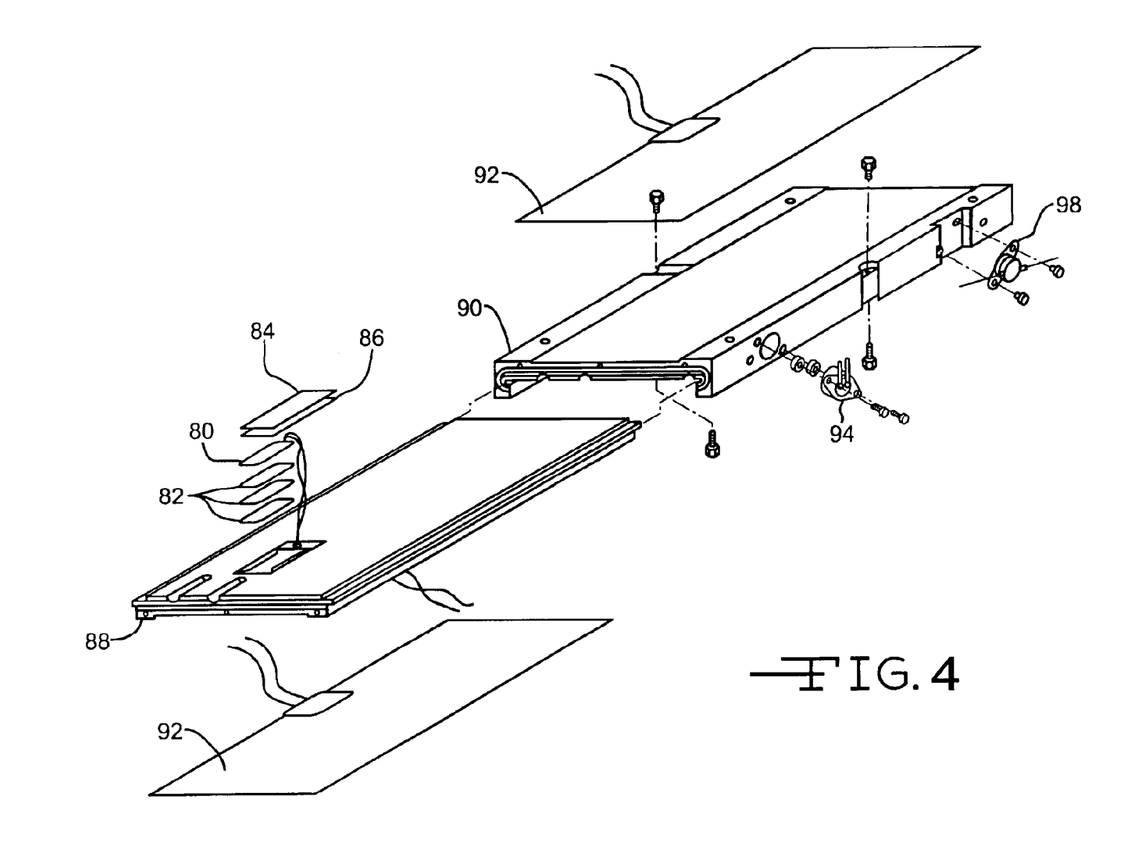
FIG. 4 is an exploded view of the internal components of the blood/fluid heater shown in FIGS. 1 and 2.
Figure 5:
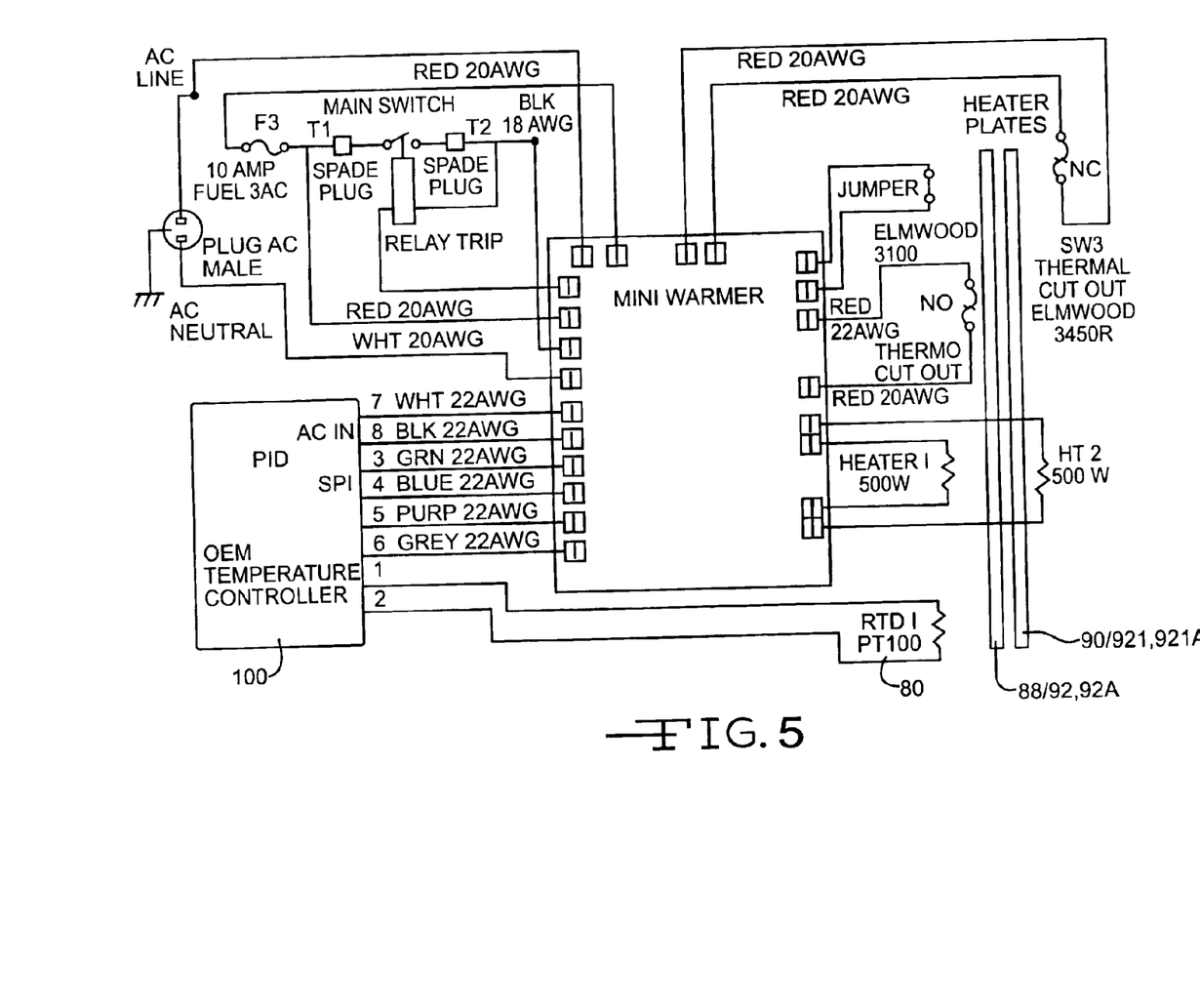
FIG. 5 is an electrical schematic and block diagram of the blood/fluid warming device of FIGS. 1 and 2.

FIG. 4 shows an exploded view of the energy reservoirs 88 and 90. There are two identical heater pads 92 vulcanized and/or adhesived to energy reservoirs 88 and 90 contained in the device 10. Preferably, one heater is located on each side of slot 12. As the bag or heat exchanger 16 is inserted into slot 12 it precisely aligns the outlet flow path portion with sensor 80. The alignment and registry between the guide rails 48 and 50 of the heat exchanger 16 and mating guide channels 22 and 24 of the device 10 guarantee this precise alignment result.

Each heater element 92, 921 can be silicone rubber and vulcanized to the respective energy reservoir 88 and 90. Each heater element 92 is a thin film, having the capacity to produce sufficient heat, for example, 500 Watts at 120 VAC input. Suitable heater elements are well known and available in the art.

Sensor 80 is a resistance temperature detector and/or a conventional thermistor located near fluid path outlet 28 of the heat exchanger. Sensor 80 is thermally insulated from the energy reservoir 88 and 90. In one embodiment the sensor 80 is covered by a layer of high temperature adhesive 86 and a thin layer of stainless steel 84. Total distance from sensor 80 to the fluid in the heat exchanger is small, like ten thousandths of an inch (0.010"). Suitable sensors are well known and available in the art.

Referring to FIG. 3, the cooler fluid enters the heat exchanger 16 at inlet port 26, flows through flow path portion 52 to the left side of heat exchanger 16 through the bottom segment 60, then through right side (farthest side) fluid path portion 54, continues to fluid path portion 56 with a 180° turn from fluid path 54, and then continues to outlet fluid path portion 58 with another 180° turn from fluid path 56. Fluid path 58 is the warmest fluid path portion and is located adjacent, for this embodiment the coldest path portion 52. The sensor 80 is located near outlet 28 where the fluid exits the heat exchanger 16.

The described sensor in its specific location is an important component to the control system. The thermal feedback system used is a proportional, integral, derivative (PID) and/or a conventional micro controller (PIC) temperature controller 100. The temperature controller operates at least one energy reservoir, and in some embodiments one set of two energy reservoirs, or multiple (3 or more) energy reservoirs. Alternatively, it is possible that each energy reservoir is controlled by a single temperature controller. In any case, the temperature controller has three fundamental functions, which are as follows: (1) dampen the system's response, (2) correct for droop in the temperature, and (3) diminish the chance of overshooting and undershooting the desired temperature. The sensor input sampling rate is 10 samples/second or any other predetermined ratio of the fluid exiting the heat exchanger 16. A thermal counterbalance of fluid exists when the heat exchanger 16 is compared to a predetermined set temperature which is the feedback signal to the temperature controller 100. The temperature controller adjusts and replenishes any energy lost to the energy reservoirs through the heater elements 92, 921.

Unlike prior primary temperature controllers, the present invention has a primary temperature controller that maintains a fluid temperature at any reasonable fluid rate to a patient. The desired fluid temperature can be anywhere between and including ambient temperature to 50 or 60° C. In addition, the primary temperature controller is set to a predetermined temperature that corresponds with the desired fluid temperature, 35° through 43° C.—called the set temperature. If the primary controller senses the fluid temperature is X° C. (wherein X can be any predetermined value, for example and not limited to any value including and between 0.1 to 5) above the set temperature, then the primary controller activates an audible and/or visual alarm and could cut off power to the energy reservoir. And if the primary controller senses the fluid temperature is X+Y° C. (wherein Y can be any predetermined value, for example and not limited to any value including and between 0.1 to 5) above the set temperature, the primary controller activates a second alarm (visual and/or audible alarm) and will shut off the power to the energy reservoir. The unit will, in a preferred embodiment, wait until the fluid temperature drops below X° C. above the set temperature before turning off the alarms and/or turning on the unit.

This embodiment is different from other primary controllers because the alarm temperatures were always predetermined, for example 43.5° C. for the first alarm and 45° C. for the second alarm. Instead of having fixed temperatures, the present invention uses variable temperature differentials from the set temperature. That way, the present invention is more efficient than the prior models.

When the primary controller senses a fluid temperature Z° C. (Z can be any predetermined value, for example and not limited to any value including and between 0.1 to 7) below the set temperature, an alarm (audible and/or visual) will be activated. In addition, the device 10 will automatically adjust power to the energy reservoir. These alarms and emergency heating will terminate when the fluid temperature rises above the set temperature−minus Z° C.

The temperature controller is recognized to be regularly available in the art except these devices do not include the adaptations to obtain the desired alarm values—X, X+Y, and Z.

To allow maximum user flexibility, especially important in emergency hospital care, a blood/fluid warming system is designed and provided in which each heat exchanger 16, 16a is inserted into a corresponding slot 12, 12a of warmer device 10. For proper operation, the heat exchanger bag 16, 16a must be completely inserted into its corresponding slot of device 10 by aligning guide rails 48 and 50 of each respective heat exchanger 16, 16a with mating slots 22 and 24, respectively, of device 10.

The apparatus 10 includes and is not limited to adding at least a second slot 12a to receive a second bag 16a and at least one corresponding heating pad 92a. These modifications to the apparatus 10 adjust the temperature uniformity and the rate of the fluid within the bag 16a and to the patient.

In one embodiment, the fluid within bag 16 and bag 16a are the same. That can occur because the conduit 200 can connect outlet 28 of bag 16 to inlet 26a of bag 16a. Accordingly, the temperature of the fluid in bags 16 and 16a can be further adjusted.

Figure 7:
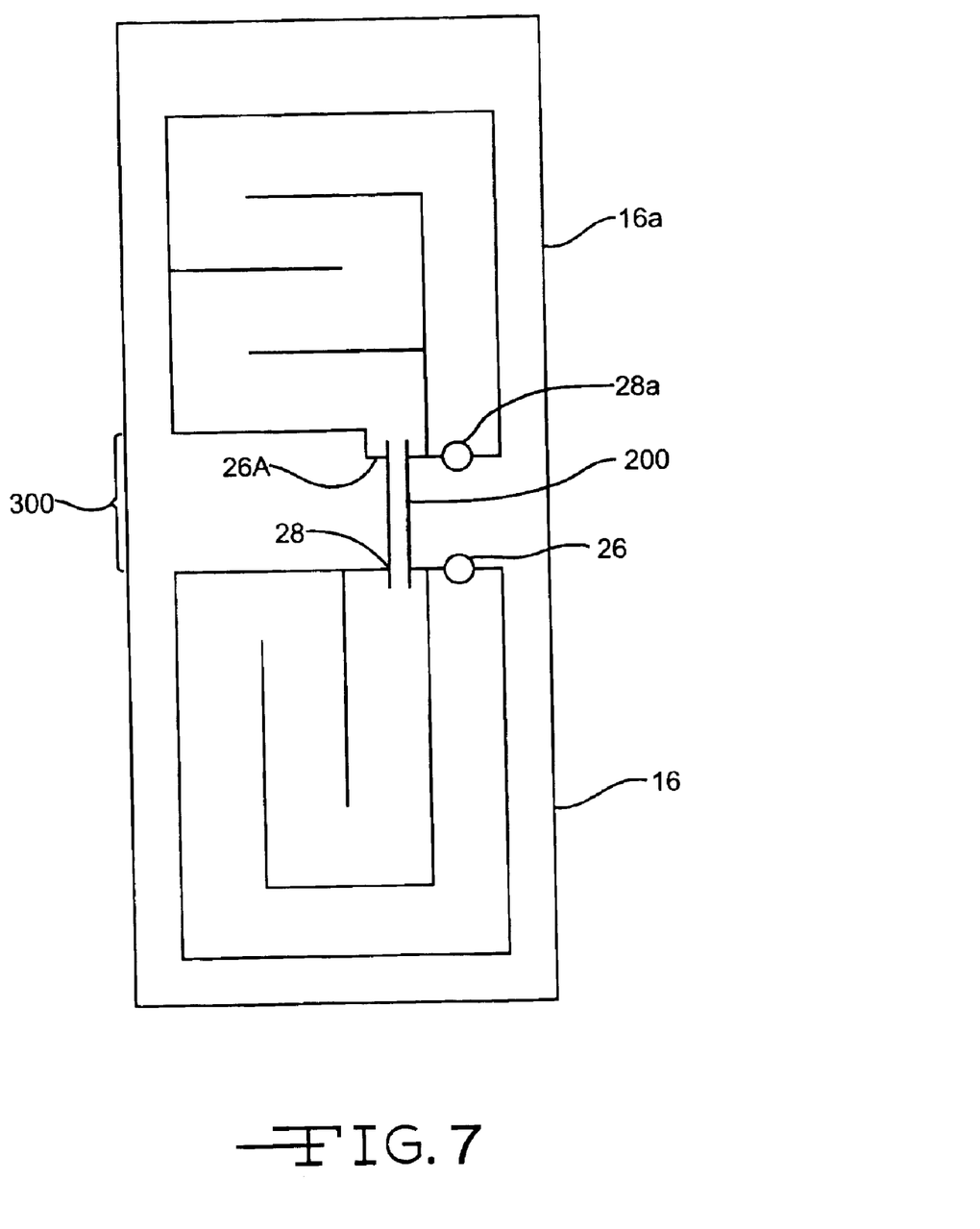
FIG. 7 is an alternative embodiment of the first and second bags as a single unit.

Alternatively, the first bag 16 and the second bag can be interconnected together at juncture 300 and be a single unit. Within the juncture can be conduit 200 which can be an integral part of the interconnected bags, as shown in FIG. 7.

Figure 6:
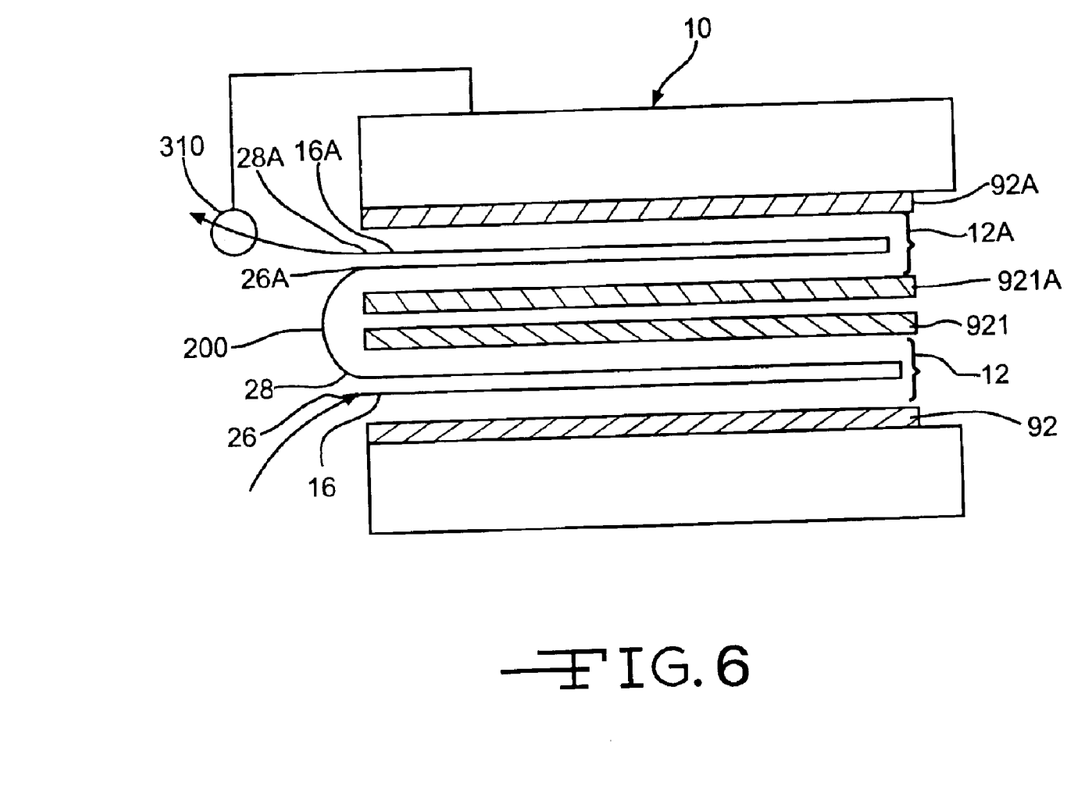
FIG. 6 is a schematic of the modifications to FIG. 1.

As stated above, slot 12 has at least one heating pad 92, positioned adjacent to the slot 12, to alter the temperature of the fluid in the bag 16 which is located within the slot. To provide more uniform fluid temperature, slot 12 is sandwiched between two energy reservoirs, identified as 92 and 921 in FIG. 6.

To increase the fluid flow and maintain the desired temperature of the fluid in apparatus 10, the inventors have positioned slot 12a between (a) heating pads 921 and 92a, (b) heating pad 921a, which is near heating pad 921, and 92a, (c) heating pads 92 and 92a, or (d) slot 12 and heating pad 92a—the former two are the preferred way. In some embodiments, the fluid contained in bags 16 and 16a could be exposed to the same temperatures or different temperatures from each energy reservoir 92, 921, 921a, and 92a, in such a way that the fluid exiting bag 16a is the desired temperature and fluid rate flow. In any of these embodiments, the fluid exiting bag 16a is the desired temperature and due to increased time within the apparatus 10, the fluid has a greater chance of maintaining the desired temperature as it flows into the patient.

In another embodiment, the apparatus 10 has a flow rate measuring device 310 that measures the flow rate of the fluid. The device 310 transmits (1) a first signal to the apparatus 10 when the flow rate exceeds a predetermined high flow rate or (2) a second signal to the apparatus 10 when the flow rate is below a predetermined low flow rate. When the apparatus receives such flow signal, it adjusts the temperature of the heater elements to obtain a desired temperature at a desired flow rate. For example, a lower temperature normally results in a higher flow rate and a higher temperature normally results in a lower flow rate. The apparatus 10 makes the appropriate adjustment to obtain the desired flow rate.

By controlling the temperature of the fluid through this double bag approach, the inventors discovered the flow rate of the fluid can be substantially increased while still obtaining the desired temperature that is delivered, at a desired flow rate, to the patient.

Alternatively, each slot 12 and 12a can operate to heat two different fluids that are within distinct bags 16 and 16a. This method is equivalent to having two apparatuses 10 side by side without obtaining the desired benefits of the present invention. Hence, this portion of the invention is not being claimed but is being disclosed as a defensive publication.

Having described the invention with regard to certain specific embodiments thereof, it is to be understood that this description is not meant as a limitation since further modifications may now suggest themselves to those skilled in the art, and it is intended to cover such modifications as fall within the scope of the appended claims.

We claim as follows:

1. A parenteral fluid warming system comprising:
   a) at least a first and a second fluid warming bag, every fluid warming bag having an inlet, an outlet, a top surface, a bottom surface, and a fluid path extending between the inlet and the outlet, wherein the coldest fluid path portion is the portion of the fluid path receiving fluid from the inlet, and the warmest fluid path portion is the portion of the fluid path providing fluid to the outlet, wherein the outlet from the first bag directs the fluid into the inlet of the second bag;
   b) a warmer device having at least a first energy reservoir and a second energy reservoir; each energy reservoir corresponds with at least one fluid warming bag, the first energy reservoir has a first heating pad and the second energy reservoir has a second heating pad, the first heating pad is capable of generating thermal energy at a different temperature in relation to the second heating pad;
   c) the top surface and/or the bottom surface of each fluid warming bag, when positioned within a respective energy reservoir, is in thermal proximity to the heating pad in the respective energy reservoir; and
   d) each heating pad generates thermal energy to provide a desired temperature to the fluid in each of at least first and second bags which are positioned within the respective at least first and second energy reservoir.

2. The parenteral fluid warming system of claim 1 wherein the fluid from the outlet of each of the first and the second fluid warming bags has a different temperature.

3. The parenteral fluid warming system of claim 1 wherein the fluid from the outlet of each of the first and the second fluid warming bags has the same temperature.

4. The parenteral fluid warning system of claim 1 wherein the first and second energy reservoirs share a common heating pad.

5. The parenteral fluid warning system of claim 1 wherein the first energy reservoir has the first heating pad and a third heating pad, and the second energy reservoir has the second heating pad and a fourth heating pad.

6. The parenteral fluid warming system of claim 5 wherein the first, second, third and fourth heating pads are independent from each other.

7. The parenteral fluid warming system of claim 5 wherein the third and the fourth heating pads are the same heating pad.

8. The parenteral fluid warming system of claim 1 wherein the first energy reservoir has the first heating pad and a third heating pads between a first slot that receives the first fluid warming bag, and the second energy reservoir has the second heating pad and a fourth heating pads between a second slot that receives the second fluid warming bag.

9. The parenteral fluid warming system of claim 1 wherein the fluid path of the fluid warming bag is tortuous.

10. The parenteral fluid warming system of claim 1 wherein the fluid path of the fluid warming bag is serpentine.

11. The parenteral fluid warming system of claim 1 further comprising a temperature controller for controlling the temperature of the fluid to a set temperature.

12. The parenteral fluid warming system of claim 11 wherein the temperature controller transmits a first alarm if the temperature of the fluid exceeds the set temperature by a predetermined first value.

13. The parenteral fluid warming system of claim 12 wherein the predetermined first value is 0.1 to 5.0° C.

14. The parenteral fluid warming system of claim 12 wherein the temperature controller transmits a second alarm if the temperature of the fluid exceeds the set temperature by a predetermined second value wherein the predetermined second value is greater than the predetermined first value.

15. The parenteral fluid warming system of claim 14 wherein the second alarm shuts down the system.

16. The parenteral fluid warming system of claim 12 wherein the first alarm shuts down the system.

17. The parenteral fluid warning system of claim 1 further comprising a third energy reservoir.

18. The parenteral fluid warming system of claim 1 wherein the fluid that is warmed in the bags to a set temperature can be delivered at any reasonable flow rate to a patient.

19. The parenteral fluid warming system of claim 1 wherein the first and second bags are a single unit.

20. The parenteral fluid warming system of claim 1 further comprising a flow rate measuring device that monitors the flow rate of the fluid.

21. The parenteral fluid warming system of claim 20 wherein the flow rate measuring device transmits a signal to the system to decrease the temperature of the fluid when the flow rate exceeds a predetermined flow rate.

22. The parenteral fluid warming system of claim 20 wherein the flow rate measuring device transmits a signal to the system to increase the temperature of the fluid when the flow rate falls below a predetermined flow rate.

* * * * *